US012667317B2

(12) United States Patent
Cheng et al.

(10) Patent No.: US 12,667,317 B2
(45) Date of Patent: Jun. 30, 2026

(54) POSITION DETECTION APPARATUS FOR WIRELESS SQUEEZE BALL, SYSTEM, AND MRI SYSTEM

(71) Applicant: Siemens Healthcare GmbH, Erlangen (DE)

(72) Inventors: Hong Cheng, Shenzhen (CN); Jianmin Wang, Shenzhen (CN); Jan Bollenbeck, Eggolsheim (DE)

(73) Assignee: Siemens Healthineers AG, Forchheim (DE)

( * ) Notice: Subject to any disclaimer, the term of this patent is extended or adjusted under 35 U.S.C. 154(b) by 148 days.

(21) Appl. No.: 18/240,379

(22) Filed: Aug. 31, 2023

(65) Prior Publication Data

US 2024/0065642 A1 Feb. 29, 2024

(30) Foreign Application Priority Data

Aug. 31, 2022 (CN) .......................... 202211061490.7

(51) Int. Cl.
*A61B 5/00* (2006.01)
*A61B 5/055* (2006.01)
(52) U.S. Cl.
CPC .............. *A61B 5/747* (2013.01); *A61B 5/055* (2013.01); *A61B 5/7475* (2013.01)
(58) Field of Classification Search
CPC .................................................. A61B 5/055
See application file for complete search history.

(56) References Cited

U.S. PATENT DOCUMENTS

| | | | | |
|---|---|---|---|---|
| 2008/0204010 A1* | 8/2008 | Crozier | .................. | G01D 9/005 |
| | | | | 324/251 |
| 2013/0119981 A1* | 5/2013 | Choi | ...................... | G01R 33/36 |
| | | | | 324/322 |
| 2017/0160367 A1* | 6/2017 | Schröter | .......... | G01R 33/56509 |
| 2018/0164392 A1* | 6/2018 | George | .................. | G01R 33/28 |
| 2018/0292502 A1* | 10/2018 | Atalar | ................ | G01R 33/3852 |
| 2020/0103479 A1* | 4/2020 | Bollenbeck | .......... | G01R 33/385 |
| 2022/0338809 A1* | 10/2022 | Sison | ..................... | A61B 5/055 |
| 2024/0404691 A1* | 12/2024 | Redder | .................. | G01R 33/28 |

* cited by examiner

*Primary Examiner* — Keith M Raymond
*Assistant Examiner* — Johnathan Maynard
(74) *Attorney, Agent, or Firm* — Banner & Witcoff, Ltd.

(57) ABSTRACT

A position detection apparatus including: an electromagnetic induction module configured to send to a mode triggering module an induced voltage signal generated due to a change in a magnetic field; a mode triggering module configured to output a preset trigger signal based on the induced voltage signal, the trigger signal corresponding to the induced voltage signal; and a signal generating module configured to generate an analog signal of a first mode corresponding to the induced voltage signal based on the received trigger signal, and send the analog signal of the first mode to an MR receiving module of an MRI system via an antenna module, so that: the MR receiving module judges whether the wireless squeeze ball has entered the interior of a body coil from outside a tubular body of the MRI system, based on the analog signal of the first mode.

18 Claims, 8 Drawing Sheets

POSITION DETECTION APPARATUS FOR WIRELESS SQUEEZE BALL, SYSTEM, AND MRI SYSTEM

TECHNICAL FIELD

The present disclosure relates to the technical field of MRI (magnetic resonance imaging), in particular to a position detection apparatus for a wireless squeeze ball, a wireless squeeze ball system, and an MRI system.

BACKGROUND

During MRI, the patient will hold a squeeze ball. The squeeze ball is the patient's safety tool: if the patient feels discomfort during the MRI scan, he can squeeze the squeeze ball to trigger a system interrupt signal to stop the MRI scanning process.

In an existing design, the squeeze ball is a rubber air balloon connected to an extremity of the MR examination table via a long air tube laid along the patient's examination table until it reaches the patient's hand. The position where the air tube is laid clashes with blankets or local coils above the patient. In addition, due to the absence of self-testing, air leakage due to the ball or air tube will result in the failure of the safety function of the squeeze ball.

The concept of a wireless squeeze ball has now been proposed; it dispenses with the air tube on the squeeze ball, making it more convenient to use.

With regard to implementing a wireless squeeze ball, there are currently three propositions:

Proposition 1: in an emergency, an alert signal is sent using a frequency of 2.4 GHz in the ISM (Industrial Scientific Medical) band, the alert signal being detectable in the system.

Proposition 2: RFID (Radio Frequency Identification) technology is used for alerting. In an emergency, the patient can squeeze the squeeze ball, causing an RFID code to change; the system detects the change in the RFID code and stops the scan.

Proposition 3: guide sound method: in an emergency, the patient squeezes the squeeze ball to generate an interference signal that can be detected by the system. This idea has the advantage that functional upgrade of existing systems is easy.

SUMMARY

In view of the above, one aspect of aspects of the present disclosure proposes a position detection apparatus for a wireless squeeze ball to enable an MRI system to promptly learn position change information of a wireless squeeze ball; another aspect proposes a wireless squeeze ball system to enable an MRI system to promptly learn position change information of a wireless squeeze ball; and another aspect proposes an MRI system, such that the MRI system can promptly learn position change information of a wireless squeeze ball.

A position detection apparatus for a wireless squeeze ball, the apparatus being located in the wireless squeeze ball, wherein the apparatus comprises: an electromagnetic induction module, a mode triggering module, a signal generating module, and an antenna module, the electromagnetic induction module and the mode triggering module being electrically connected, the mode triggering module and the signal generating module being electrically connected, and the signal generating module and the antenna module being electrically connected, wherein:

the electromagnetic induction module is configured to send to the mode triggering module an induced voltage signal generated due to a change in magnetic field;

the mode triggering module is configured to output a preset trigger signal based on the induced voltage signal sent by the electromagnetic induction module, the trigger signal corresponding to the induced voltage signal;

the signal generating module is configured to generate an analog signal of a first mode corresponding to the induced voltage signal based on the received trigger signal and send the analog signal of the first mode to an MR receiving module of a magnetic resonance imaging (MRI) system via the antenna module at a first frequency, so that: the MR receiving module judges whether the wireless squeeze ball has entered the interior of a body coil from outside a tubular body of the MRI system, based on the analog signal of the first mode, wherein the first frequency is different from an MR signal frequency.

The electromagnetic induction module is a Hall effect sensor or a reed switch.

The electromagnetic induction module comprises: a B0 field electromagnetic inductor, a low-pass filter, and an amplifier, the B0 field electromagnetic inductor and the low-pass filter being electrically connected, the low-pass filter and the amplifier being electrically connected, and the amplifier and the mode triggering module being electrically connected, wherein:

the B0 field electromagnetic inductor is configured to detect a change in magnetic flux inside a coil and send an induced voltage signal generated due to the change in magnetic flux to the amplifier via the low-pass filter;

the amplifier is configured to amplify the voltage signal processed by the low-pass filter and send the amplified voltage signal to the mode triggering module.

The B0 field electromagnetic inductor and the antenna module share a coil.

The operation of the mode triggering module outputting a preset trigger signal based on the induced voltage signal sent by the electromagnetic induction module, the trigger signal corresponding to the induced voltage signal comprises:

the mode triggering module receiving the induced voltage signal sent by the electromagnetic induction module, generating a digital signal of a first mode based on a pre-configured digital signal of a first mode corresponding to the induced voltage signal of the electromagnetic induction module, and sending the digital signal of the first mode to the signal generating module;

the operation of the signal generating module generating an analog signal of a first mode corresponding to the induced voltage signal based on the received trigger signal, comprises:

the signal generating module receiving the digital signal of the first mode sent by the mode triggering module, and converting the digital signal of the first mode into a corresponding analog signal of a first mode.

The mode triggering module is further configured to periodically generate a digital signal of a second mode based on a pre-configured digital signal of a second mode, and send the generated digital signal of the second mode to the signal generating module;

and the signal generating module is further configured to convert the digital signal of the second mode sent by the mode triggering module into an analog signal of a second mode, and send the analog signal of the second mode to the MR receiving module of the MRI system via the antenna module at a second frequency, so that: the MR receiving module judges whether the wireless squeeze ball has been taken out of a scanning room based on the analog signal of the second mode, wherein the second frequency is different from the MR signal frequency and the first frequency.

The apparatus further comprises: a wirelessly charged battery, the wirelessly charged battery being electrically connected to the mode triggering module and the signal generating module separately.

The wirelessly charged battery comprises: a supercapacitor and a voltage detector connected in parallel with the supercapacitor, the voltage detector sending a detected voltage of the supercapacitor to the mode triggering module;

the mode triggering module is further configured to output a preset trigger signal based on the voltage sent by the voltage detector, the trigger signal corresponding to the voltage, and the signal generating module generates an analog signal of a mode corresponding to the voltage sent by the voltage detector based on the trigger signal outputted by the mode triggering module, and sends the analog signal of this mode to the MR receiving module of the MRI system via the antenna module at a first frequency, so that: the MR receiving module judges a state of the wirelessly charged battery based on the analog signal of this mode.

The operation of the mode triggering module outputting a preset trigger signal based on the voltage sent by the voltage detector, the trigger signal corresponding to the voltage, comprises:

the mode triggering module receiving the voltage sent by the voltage detector, and upon detecting that the voltage is less than a preset threshold, determining that the charge level of the wirelessly charged battery is insufficient, generating a digital signal of a third mode based on a pre-configured digital signal of a third mode corresponding to insufficient charge level of the wirelessly charged battery, and sending the digital signal of the third mode to the signal generating module;

the operation of the signal generating module generating an analog signal of a mode corresponding to the voltage sent by the voltage detector based on the trigger signal outputted by the mode triggering module, comprises:

the signal generating module receiving the digital signal of the third mode sent by the mode triggering module, and converting the digital signal of the third mode into a corresponding analog signal of a third mode.

A position detection apparatus for a wireless squeeze ball, the apparatus being located in the wireless squeeze ball, wherein the apparatus comprises: a mode triggering module, a signal generating module and an antenna module, the mode triggering module and the signal generating module being electrically connected, and the signal generating module and the antenna module being electrically connected, wherein:

the mode triggering module is configured to periodically generate a digital signal of a second mode based on a pre-configured digital signal of a second mode, and send the generated digital signal of the second mode to the signal generating module;

the signal generating module is configured to convert the digital signal of the second mode sent by the mode triggering module into an analog signal of a second mode, and send the analog signal of the second mode to an MR receiving module of a magnetic resonance imaging (MRI) system via the antenna module at a second frequency, so that: the MR receiving module judges whether the wireless squeeze ball has been taken out of a scanning room based on the analog signal of the second mode, wherein the second frequency is different from an MR signal frequency.

The apparatus further comprises: a wirelessly charged battery, the wirelessly charged battery being electrically connected to the mode triggering module and the signal generating module separately.

The wirelessly charged battery comprises: a supercapacitor and a voltage detector connected in parallel with the supercapacitor, the voltage detector sending a detected voltage of the supercapacitor to the mode triggering module;

the mode triggering module is further configured to output a preset trigger signal based on the voltage sent by the voltage detector, the trigger signal corresponding to the voltage, and the signal generating module generates an analog signal of a mode corresponding to the voltage sent by the voltage detector based on the trigger signal outputted by the mode triggering module, and sends the analog signal of this mode to the MR receiving module of the MRI system via the antenna module at a first frequency, so that: the MR receiving module judges a state of the wirelessly charged battery based on the analog signal of this mode.

The operation of the mode triggering module outputting a preset trigger signal based on the voltage sent by the voltage detector, the trigger signal corresponding to the voltage, comprises:

the mode triggering module receiving the voltage sent by the voltage detector, and upon detecting that the voltage is less than a preset threshold, determining that the charge level of the wirelessly charged battery is insufficient, generating a digital signal of a third mode based on a pre-configured digital signal of a third mode corresponding to insufficient charge level of the wirelessly charged battery, and sending the digital signal of the third mode to the signal generating module;

the operation of the signal generating module generating an analog signal of a mode corresponding to the voltage sent by the voltage detector based on the trigger signal outputted by the mode triggering module, comprises:

the signal generating module receiving the digital signal of the third mode sent by the mode triggering module, and converting the digital signal of the third mode into a corresponding analog signal of a third mode.

A wireless squeeze ball system, wherein the system comprises: a wireless charging apparatus and a wireless squeeze ball, wherein the wireless squeeze ball comprises the position detection apparatus for a wireless squeeze ball as described in any one of the aspects above.

The wireless charging apparatus comprises: a voltage converter, an oscillator and a charging module, the voltage converter and the oscillator being electrically connected, and the oscillator and the charging module being electrically connected, wherein:

the voltage converter is configured to convert a voltage of a received external power signal to a voltage of a wirelessly charged battery, and send the converted power signal to the oscillator;

the oscillator is configured to transmit the power signal sent by the voltage converter, to the wirelessly charged battery of the wireless squeeze ball in the charging module.

The charging module uses a capacitive power transfer (CPT) system.

The charging module comprises: at least one oscillation circuit, a rectifier and a low-dropout regulator (LDO); a resonant frequency of each oscillation circuit separately corresponds to a transmission frequency of a wireless charging transmission coil; after series connection of the at least one oscillation circuit, the two ends thereof are separately connected to AC input ends of the rectifier, a DC output end of the rectifier is connected to an input end of the LDO, and an output end of the LDO is connected to the wirelessly charged battery, wherein:

each oscillation circuit is configured to separately receive a power signal sent by the wireless charging transmission coil of the corresponding frequency and output the power signal to the rectifier;

the rectifier is configured to convert an AC signal outputted by the oscillation circuit into a DC signal, and send the converted DC signal to the LDO;

the LDO is configured to convert a voltage of the DC signal outputted by the rectifier into a voltage of the wirelessly charged battery and then output same to the wirelessly charged battery.

An MRI system, comprising the position detection apparatus for a wireless squeeze ball as described in any one of the aspects above, or comprising the wireless squeeze ball system as described in any one of the aspects above.

In aspects of the present disclosure, as a result of providing the wireless squeeze ball position detection apparatus in the wireless squeeze ball, the MRI system is enabled to promptly learn position change information of the wireless squeeze ball, helping to improve the MRI system's operating efficiency as well as the patient's experience, specifically as a result of the fact that the electromagnetic induction module in the apparatus sends to the mode triggering module an induced voltage signal generated due to a change in magnetic field, the mode triggering module outputs a preset trigger signal based on the induced voltage signal sent by the electromagnetic induction module, the trigger signal corresponding to the induced voltage signal, and the signal generating module generates an analog signal of a first mode corresponding to the induced voltage signal based on the received trigger signal, and sends the analog signal of the first mode to the MR receiving module of the MRI system via the antenna module, so that: the MR receiving module judges whether the wireless squeeze ball has entered the interior of the body coil from outside the tubular body of the MRI system, based on the analog signal of the first mode.

BRIEF DESCRIPTION OF THE DRAWINGS

Preferred aspects of the present disclosure are described in detail below with reference to the drawings to give those skilled in the art a clearer understanding of the abovementioned and other features and advantages of the present disclosure. In the figures.

KEY TO THE DRAWINGS

| Reference sign | Meaning |
| --- | --- |
| 10, 20 | Position detection apparatus for wireless squeeze ball |
| 11 | Electromagnetic induction module |
| 12, 21 | Mode triggering module |
| 13, 22 | Signal generating module |
| 14, 23 | Antenna module |
| 211 | 3D Hall effect module |
| 212 | MUX |
| 213 | Amplification and filtering module |
| 214 | Analog-to-digital conversion module |
| 215 | Interface module |
| 216 | Power management and oscillator module |
| 217 | Temperature sensor |
| 218 | Configuration registration module |
| 219 | Result registration module |
| 220 | Digital operation unit |
| 021 | Power pin |
| 022 | Test pin |
| 023 | Clock pin |
| 024 | Data pin |
| 025 | Interrupt pin |
| 026 | Ground pin |
| 31 | Analog bipolar Hall effect sensor in SOT23 package form |
| 32 | Analog bipolar Hall effect sensor in SIP package form |
| 311, 321 | Power pin |
| 312, 322 | Ground pin |
| 313, 323 | Output pin |
| 411 | B0 field electromagnetic inductor |
| 412 | Low-pass filter |
| 413 | Amplifier |
| 15, 24 | Wirelessly charged battery |
| 81 | Wireless charging apparatus |
| 811 | Voltage converter |
| 812 | Oscillator |
| 813 | Charging module |
| 911 | Inverter |
| 912 | First compensation circuit |
| 913 | Capacitive coupling circuit |
| 914 | Second compensation circuit |
| 915 | Rectifier |
| 1011, 1012 | Oscillation circuit |
| 1013 | Rectifier |
| 1014 | LDO |

DETAILED DESCRIPTION

To clarify the objective, technical solution, and advantages of the present disclosure, the present disclosure is explained in further detail below by way of aspects.

In an analysis of the three existing propositions for implementing a wireless squeeze ball, the inventors have found the following shortcomings:

They all focus on how to detect whether the wireless squeeze ball is squeezed, paying no attention to the position of the wireless squeeze ball. In fact, because a wireless squeeze ball is wireless, it can be moved very easily. Hence, detection of its position is very important for an MRI process, for example: whether the wireless squeeze ball is already located inside the body coil when an MRI scanning stage is about to begin, whether the wireless squeeze ball is taken out of the scanning room unintentionally by the patient or someone else when the MRI scanning stage ends; and so on. These all directly impact whether the MRI scanning process can start and proceed normally.

Figure 1:
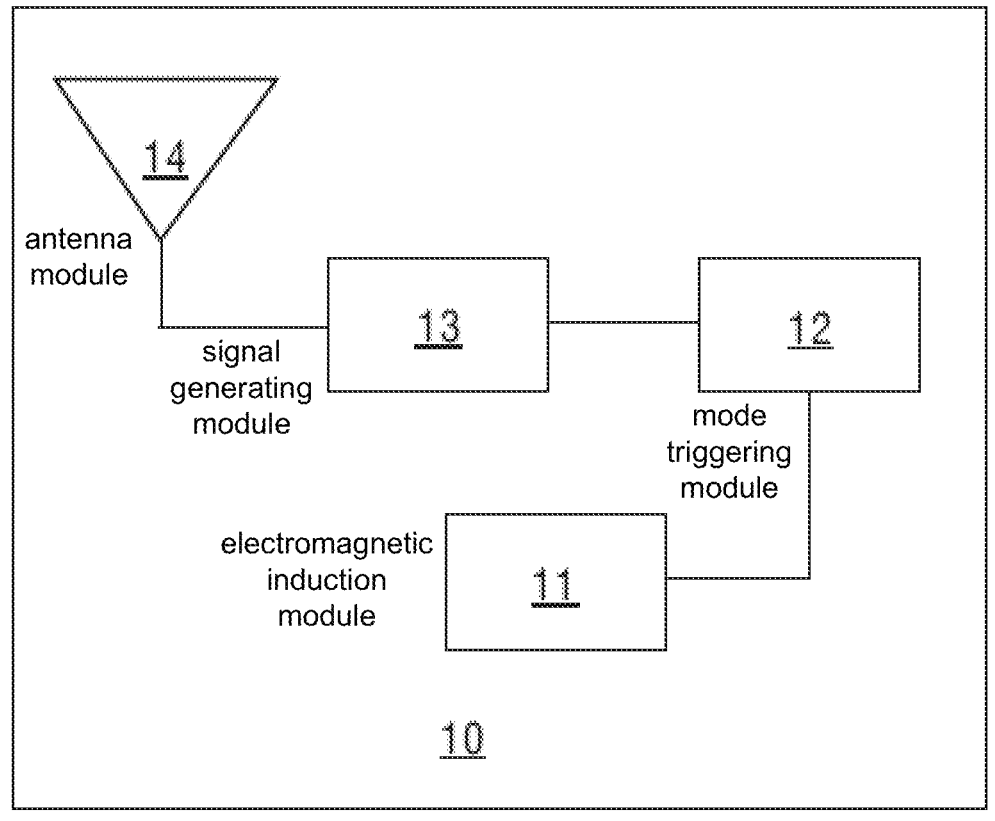
FIG. 1 is a schematic structural diagram of a position detection apparatus for a wireless squeeze ball, as provided in a first aspect of the present disclosure.

FIG. 1 is a schematic structural diagram of a position detection apparatus 10 for a wireless squeeze ball, as provided in a first aspect of the present disclosure. The apparatus 10 is located in the squeeze ball, and the apparatus 10 mainly comprises: an electromagnetic induction module 11, a mode triggering module 12, a signal generating module 13, and an antenna module 14, wherein: the electromagnetic induction module 11 and mode triggering module 12 are electrically connected, the mode triggering module 12 and signal generating module 13 are electrically connected, and the signal generating module 13 and antenna module 14 are electrically connected, wherein:

The electromagnetic induction module 11 is configured to send to the mode triggering module 12 an induced voltage signal generated due to a change in magnetic field.

The mode triggering module 12 is configured to output a preset trigger signal based on the induced voltage signal sent by the electromagnetic induction module 11, the trigger signal corresponding to the induced voltage signal, and send the trigger signal to the signal generating module 13.

The signal generating module 13 is configured to generate an analog signal of a first mode corresponding to the induced voltage signal based on the received trigger signal and send the analog signal of the first mode to an MR receiving module of an MRI system via the antenna module 14 at a first frequency, so that: the MR receiving module judges whether the wireless squeeze ball has entered the interior of a body coil from outside a tubular body of the MRI system, based on the analog signal of the first mode, wherein the first frequency is different from an MR signal frequency.

For example, the first frequency at which the signal generating module 13 sends the analog signal of the first mode may be 63.6 MHz or 62.5 MHz or 27 MHz. After being sent out via the antenna module 14, the analog signal of the first mode may be received by a local coil or body coil of the MRI system and transmitted to the MR receiving module of the MRI system.

In the aspect described above, as a result of providing the wireless squeeze ball position detection apparatus in the wireless squeeze ball, the MRI system is enabled to promptly learn position change information of the wireless squeeze ball, helping to improve the MRI system's operating efficiency as well as the patient's experience, specifically as a result of the fact that the electromagnetic induction module in the apparatus sends to the mode triggering module an induced voltage signal generated due to a change in magnetic field, the mode triggering module outputs a preset trigger signal based on the induced voltage signal sent by the electromagnetic induction module, the trigger signal corresponding to the induced voltage signal, and the signal generating module generates an analog signal of a first mode corresponding to the induced voltage signal based on the received trigger signal, and sends the analog signal of the first mode to the MR receiving module of the MRI system via the antenna module, so that: the MR receiving module judges whether the wireless squeeze ball has entered the interior of the body coil from outside the tubular body of the MRI system, based on the analog signal of the first mode.

In an optional aspect, the electromagnetic induction module 11 is: a Hall effect sensor.

The Hall effect sensor may be a 3D (3-dimensional) Hall effect sensor.

Figure 2:
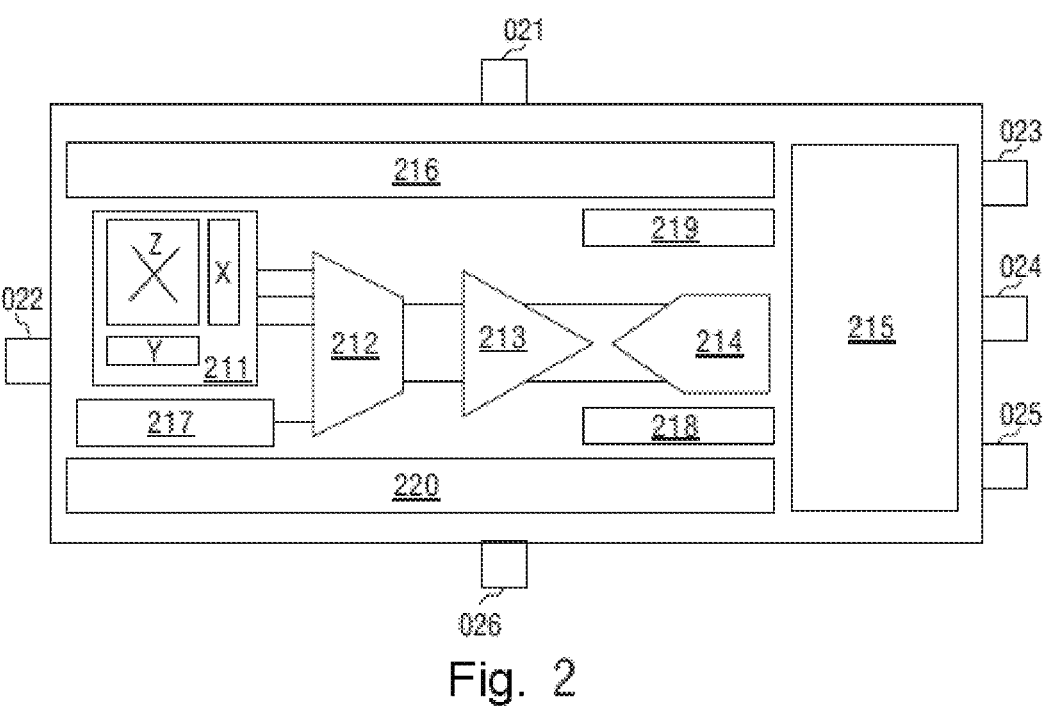
FIG. 2 is a schematic structural diagram of an existing 3D Hall effect sensor chip with model number TMAG5273.

FIG. 2 is a schematic structural diagram of an existing 3D (3-dimensional) Hall effect sensor chip with model number TMAG5273. The chip uses a SOT (Small Outline Transistor) 23 package, with a maximum height of just 1.45 mm (millimeters), mainly comprising: a 3D Hall effect module 211, a MUX (multiplexer) 212, an amplification and filtering module 213, an analog-to-digital conversion module 214 and an interface module 215. Here:

The 3D Hall effect module 211 is configured to sense magnetic field changes in X, Y, and Z axis directions and separately send induced voltage signals generated by the magnetic field changes in the X, Y, and Z axis directions to the MUX 212.

The MUX 212 is configured to send the received voltage signals to the amplification and filtering module 213.

The amplification and filtering module 213 is configured to amplify and filter the received voltage signals and then send them to the analog-to-digital conversion module 214.

The analog-to-digital conversion module 214 is configured to subject the received voltage signals to analog-to-digital conversion and then transmit them to the mode triggering module 12 via the interface module 215.

As shown in FIG. 2, the TMAG5273 chip further comprises a power management and oscillator module 216, a temperature sensor 217, a configuration registration module 218, a result registration module 219, and a digital operation unit 220. 021 is a power pin, 022 is a test pin, 023 is a clock pin, 024 is a data pin, 025 is an interrupt pin, and 026 is a ground pin.

The Hall effect sensor may also be an analog-bipolar Hall effect sensor, typically an analog-bipolar Hall effect sensor chip with model number DRV5053, for example; this chip has the advantage of being fully analog and being able to run without the need for an MCU (microcontroller unit) or FPGA (field programmable gate array).

Figure 3:
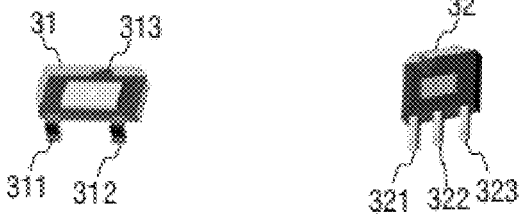
FIG. 3 is a schematic diagram of existing analog bipolar Hall effect sensor packages.

FIG. 3 is a schematic diagram of existing analog bipolar Hall effect sensor packages, wherein 31 is in the SOT23 package form, whereas 32 is in the SIP (System In a Package) package form. 311, 321 are power pins; 312, 322 are ground pins; 313, 323 are output pins.

In an optional aspect, the electromagnetic induction module is: a reed switch. The reed switch closes after sensing a magnetic field; a voltage signal between the reeds is outputted to the mode triggering module 12; the mode triggering module 12 outputs a preset trigger signal based on the voltage signal outputted by the reed switch, the trigger signal corresponding to the voltage signal, and the signal generating module 13 generates an analog signal of a first mode corresponding to the voltage signal based on the received trigger signal. After the analog signal of the first mode reaches an MR receiver, the MR receiver decodes the analog signal of the first mode and can then judge that the reeds are closed to determine a corresponding magnetic field change and then determine whether the wireless squeeze ball has entered the interior of the body coil from outside the tubular body of the MRI system.

Figure 4:
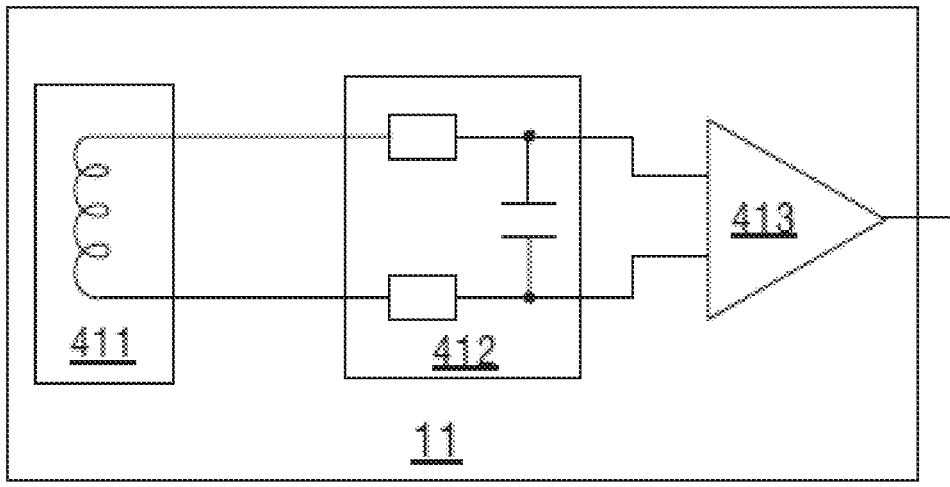
FIG. 4 is a schematic structural diagram of an electromagnetic induction module provided in an aspect of the present disclosure.

FIG. 4 is a schematic structural diagram of the electromagnetic induction module 11 provided in an aspect of the present disclosure, mainly comprising: a B0 field electromagnetic inductor 411, a low-pass filter 412, and an amplifier 413. The B0 field electromagnetic inductor 411 and the low-pass filter 412 are electrically connected, and the low-pass filter 412 and the amplifier 413 are electrically connected. The amplifier 413 and the mode triggering module 12 are electrically connected, wherein:

the B0 field electromagnetic inductor 411 is configured to detect a change in magnetic flux inside a coil and send an induced voltage signal generated due to the change in magnetic flux to the amplifier 413 via the low-pass filter 412;

the amplifier 413 is configured to amplify the voltage signal processed by the low-pass filter 412 and send the amplified voltage signal to the mode triggering module 12.

When the loop diameter of the coil is 2 cm (centimeters), and the rate of change is 500 mT/s (milliteslas/second), an induced voltage signal will be generated in the sub-mV (millivolt) region, and the coil used in aspects of the present disclosure conforms to this index; therefore, the induced voltage signal needs to be amplified.

In an optional aspect, the B0 field electromagnetic inductor 411 may share a coil with the antenna module 14 to reduce the overall size of the wireless squeeze ball position detection apparatus 10. In actual application, the B0 field electromagnetic inductor 411 may be placed in an RF shield.

In an optional aspect, the operation of the mode triggering module 12 outputting a preset trigger signal based on the induced voltage signal sent by the electromagnetic induction module 11, the trigger signal corresponding to the induced voltage signal, comprises: the mode triggering module 12 receiving the induced voltage signal sent by the electromagnetic induction module 11, generating a digital signal of a first mode based on a pre-configured digital signal of a first mode corresponding to the induced voltage signal of the electromagnetic induction module 11, and sending the digital signal of the first mode to the signal generating module 13;

and the operation of the signal generating module 13 generating an analog signal of a first mode corresponding to the induced voltage signal based on the received trigger signal, comprises: the signal generating module 13 receiving the digital signal of the first mode sent by the mode triggering module 12, and converting the digital signal of the first mode into a corresponding analog signal of a first mode. For example, if the digital signal of the first mode is 010101 . . . , then the corresponding analog signal of the first mode is a signal of LOW HIGH LOW HIGH LOW HIGH . . . level.

In an optional aspect, after receiving the induced voltage signal sent by the electromagnetic induction module 11, the mode triggering module 12 can first judge whether the voltage of the induced voltage signal is greater than a preset first threshold, and, if so, generate a digital signal of a first mode based on a pre-configured digital signal of a first mode corresponding to the induced voltage signal of the electromagnetic induction module 11; otherwise, no further processing is performed.

Upon receiving the analog signal of the first mode sent by the wireless squeeze ball position detection apparatus 10, the MR receiving module of the MRI system analyses the analog signal of the first mode, learning that the signal indicates that the wireless squeeze ball has entered the interior of the body coil from outside the tubular body. The MR receiving module can judge whether an alert should be sent and what kind of alert to send in the case where an alert should be sent, based on the current position of the wireless squeeze ball as well as the scanning state of the MRI system or/and a squeezing state of the wireless squeeze ball. For example: if the system is currently in a stage in which an MRI scan is about to begin, but the wireless squeeze ball is still not inside the body coil, an alert that the wireless squeeze ball is not inside the body coil is sent; if the system is in the process of an MRI scan, and the wireless squeeze ball is located inside the body coil, and a squeezing signal sent by a squeezing detection module of the wireless squeeze ball is received, then it is determined that the patient has squeezed the squeeze ball, so an alert to interrupt the MRI scan is sent.

In an optional aspect, the mode triggering module 12 is further configured to periodically generate a digital signal of a second mode based on a pre-configured digital signal of a second mode, and send the generated digital signal of the second mode to the signal generating module 13;

and the signal generating module 13 is further configured to convert the digital signal of the second mode sent by the mode triggering module 12 into an analog signal of a second mode, and send the analog signal of the second mode to the MR receiving module of the MRI system via the antenna module 14 at a second frequency, so that: the MR receiving module judges whether the wireless squeeze ball has been taken out of the scanning room based on the analog signal of the second mode, wherein the second frequency is different from the MR signal frequency and the first frequency.

Specifically, if the MR receiving module does not receive an analog signal of a second mode within a continuous preset length of time, then it is determined that the wireless squeeze ball has been taken out of the scanning room, and an alert that the wireless squeeze ball has been taken out of the scanning room is sent.

Figure 5:
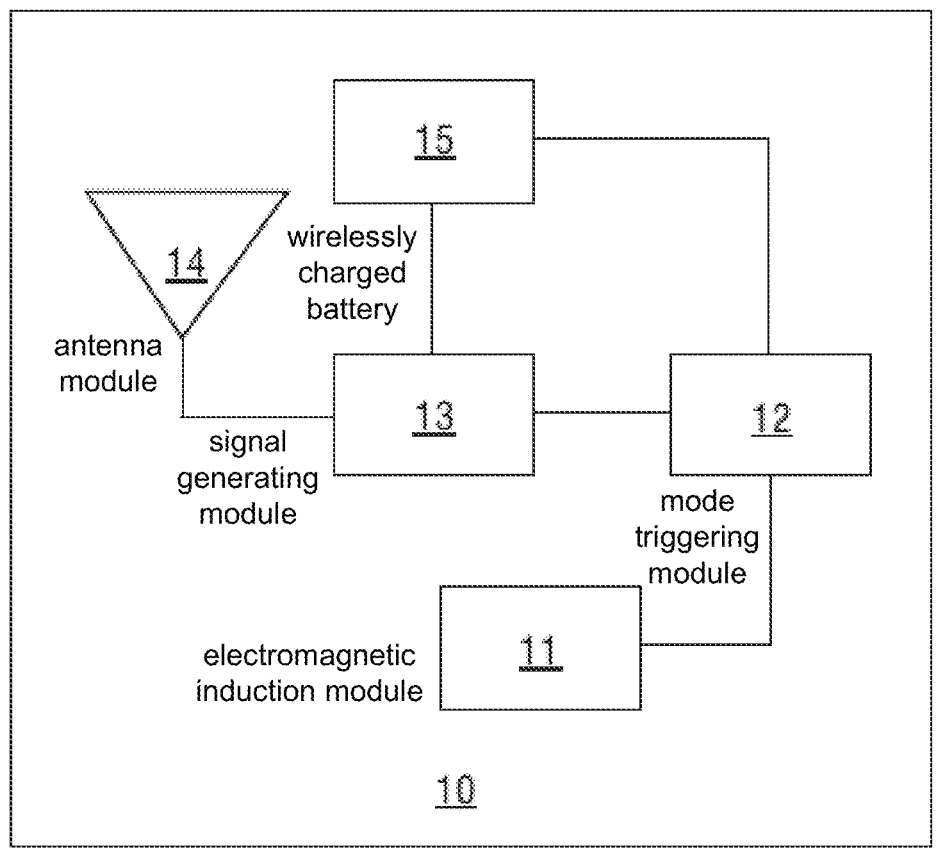
FIG. 5 is a schematic structural diagram of a position detection apparatus for a wireless squeeze ball, as provided in a second aspect of the present disclosure.

FIG. 5 is a schematic structural diagram of a position detection apparatus 10 for a wireless squeeze ball, as provided in a second aspect of the present disclosure. Compared with the first aspect, in this aspect, a wirelessly charged battery 15 is added, the wirelessly charged battery 15 being electrically connected to the mode triggering module 12 and the signal generating module 13 separately.

In an optional aspect, the wirelessly charged battery 15 comprises: a supercapacitor and a voltage detector connected in parallel with the supercapacitor, wherein the voltage detector sends a detected voltage of the supercapacitor to the mode triggering module 12;

the mode triggering module 12 is further configured to output a preset trigger signal based on the voltage sent by the voltage detector, the trigger signal corresponding to the voltage, and the signal generating module 13 generates an analog signal of a mode corresponding to the voltage sent by the voltage detector based on the trigger signal outputted by the mode triggering module 12, and sends the analog signal of this mode to the MR receiving module of the MRI system via the antenna module 14 at a first frequency, so that: the MR receiving module judges a state of the wirelessly charged battery 15 based on the analog signal of this mode.

In an optional aspect, the operation of the mode triggering module 12 outputting a preset trigger signal based on the voltage sent by the voltage detector, the trigger signal corresponding to the voltage, comprises: the mode triggering module 12 receiving the voltage sent by the voltage detector, and upon detecting that the voltage is less than a preset second threshold, determining that the charge level of the wirelessly charged battery 15 is insufficient, generating a digital signal of a third mode based on a pre-configured digital signal of a third mode corresponding to insufficient charge level of the wirelessly charged battery 15, and sending the digital signal of the third mode to the signal generating module 13;

and the operation of the signal generating module 13 generating a mode analog signal corresponding to the voltage sent by the voltage detector based on the trigger signal outputted by the mode triggering module 12, comprises: the signal generating module 13 receiving the digital signal of the third mode sent by the mode triggering module 12, and converting the digital signal of the third mode into a corresponding analog signal of a third mode.

Figure 6:
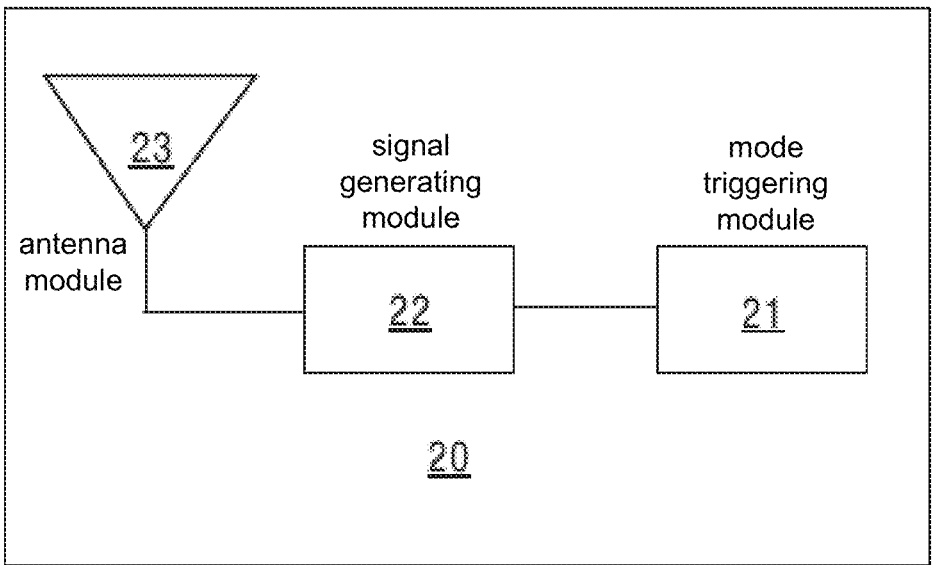
FIG. 6 is a schematic structural diagram of a position detection apparatus for a wireless squeeze ball, as provided in a third aspect of the present disclosure.

FIG. 6 is a schematic structural diagram of a position detection apparatus 20 for a wireless squeeze ball, as provided in a third aspect of the present disclosure. The apparatus 20 is located in the wireless squeeze ball. The apparatus 20 mainly comprises: a mode triggering module 21, a signal generating module 22 and an antenna module 23, the mode triggering module 21 and signal generating module 22 being electrically connected, and the signal generating module 22 and antenna module 23 being electrically connected, wherein:

the mode triggering module 21 is configured to periodically generate a digital signal of a second mode based on a pre-configured digital signal of a second mode, and send the generated digital signal of the second mode to the signal generating module 22.

The signal generating module 22 is configured to convert the digital signal of the second mode sent by the mode triggering module 21 into an analog signal of a second mode, and send the analog signal of the second mode to the MR receiving module of the MRI system via the antenna module 23 at a second frequency, so that: the MR receiving module judges whether the wireless squeeze ball has been taken out of the scanning room based on the analog signal of the second mode, wherein the second frequency is different from an MR signal frequency.

Figure 7:
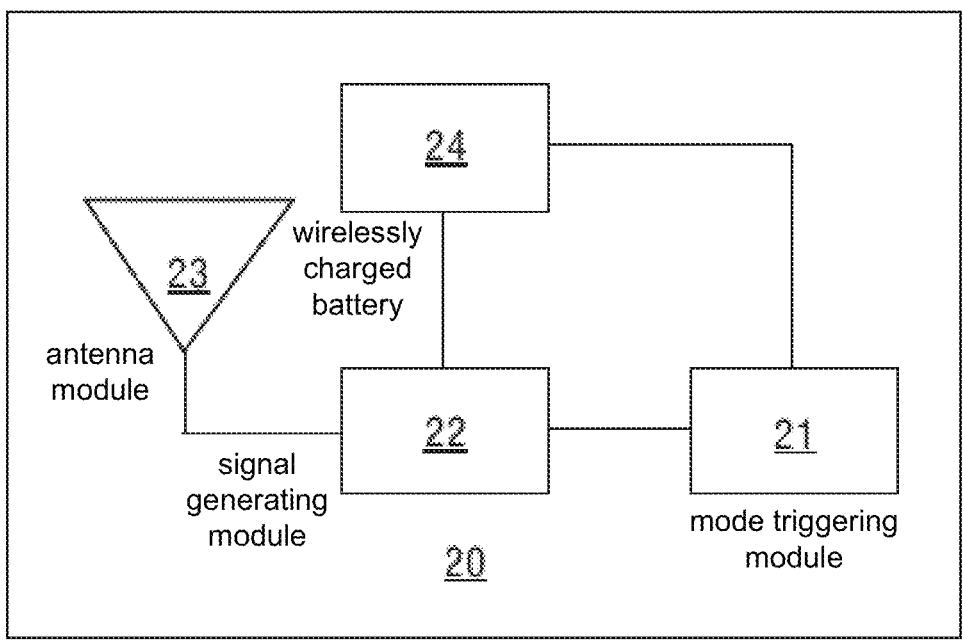
FIG. 7 is a schematic structural diagram of a position detection apparatus for a wireless squeeze ball, as provided in a fourth aspect of the present disclosure.

FIG. 7 is a schematic structural diagram of a position detection apparatus 20 for a wireless squeeze ball, as provided in a fourth aspect of the present disclosure. Compared with the third aspect, a wirelessly charged battery 24 is added, the wirelessly charged battery 24 being electrically connected to the mode triggering module 21 and the signal generating module 22 separately.

In an optional aspect, the wirelessly charged battery 24 comprises: a supercapacitor and a voltage detector connected in parallel with the supercapacitor, wherein the voltage detector sends a detected voltage of the supercapacitor to the mode triggering module 21;

and the mode triggering module 21 is further configured to output a preset trigger signal based on the voltage sent by the voltage detector, the trigger signal corresponding to the voltage, and the signal generating module 22 generates an analog signal of a mode corresponding to the voltage sent by the voltage detector based on the trigger signal outputted by the mode triggering module 21, and sends the analog signal of this mode to the MR receiving module of the MRI system via the antenna module 23 at a first frequency, so that: the MR receiving module judges a state of the wirelessly charged battery 24 based on the analog signal of this mode.

In an optional aspect, the operation of the mode triggering module 21 outputting a preset trigger signal based on the voltage sent by the voltage detector, the trigger signal corresponding to the voltage, comprises: the mode triggering module 21 receiving the voltage sent by the voltage detector, and upon detecting that the voltage is less than a preset second threshold, determining that the charge level of the wirelessly charged battery 24 is insufficient, generating a digital signal of a third mode based on a pre-configured digital signal of a third mode corresponding to insufficient charge level of the wirelessly charged battery 24, and sending the digital signal of the third mode to the signal generating module 22;

and the operation of the signal generating module 22 generating a mode analog signal corresponding to the voltage sent by the voltage detector based on the trigger signal outputted by the mode triggering module 21, comprises: the signal generating module 22 receiving the digital signal of the third mode sent by the mode triggering module 21, and converting the digital signal of the third mode into a corresponding analog signal of a third mode.

Aspects of the present disclosure further provide a wireless squeeze ball system comprising a wireless charging apparatus and a wireless squeeze ball, wherein the wireless squeeze ball comprises the wireless squeeze ball position detection apparatus 10 as described above, or the wireless squeeze ball comprises the wireless squeeze ball position detection apparatus 20 as described above.

Figure 8:
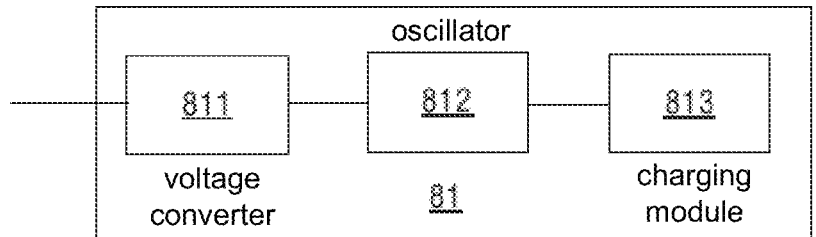
FIG. 8 is a schematic structural diagram of a wireless charging apparatus provided in an aspect of the present disclosure.

FIG. 8 is a schematic structural diagram of a wireless charging apparatus 81 provided in an aspect of the present disclosure, mainly comprising: a voltage converter 811, an oscillator 812 and a charging module 813, the voltage converter 811 and oscillator 812 are electrically connected, and the oscillator 812 and charging module 813 is electrically connected, wherein:

the voltage converter 811 is configured to receive an external power signal, convert a voltage of the external power signal to a voltage of the wirelessly charged battery 15 or wirelessly charged battery 24, and send the converted power signal to the oscillator 812;

the oscillator 812 is configured to use an internal oscillation circuit to transmit the power signal sent by the voltage converter 811 to the wirelessly charged battery 15 or wirelessly charged battery 24 of the wireless squeeze ball in the charging module 813.

The resonant frequency of the oscillator 812 should not interfere with the MR signal; for example: in actual application, the resonant frequency of the oscillator 812 may be 2.5 MHz.

As an optional aspect, the charging module 813 uses a CPT (Capacitive Power Transfer) system.

Figure 9:
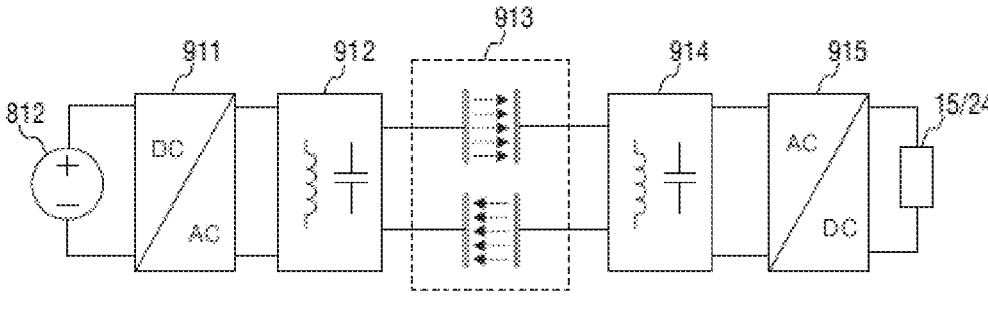
FIG. 9 is a schematic structural diagram of a typical CPT system.

FIG. 9 is a schematic structural diagram of a typical CPT system. As shown in FIG. 9, it mainly comprises: an inverter 911, a first compensation circuit 912, a capacitive coupling circuit 913, a second compensation circuit 914, and a rectifier 915, wherein:

the inverter 911 is configured to convert a DC signal outputted by the oscillator 812 into an AC signal of a set frequency and output the AC signal to the first compensation circuit 912;

the first compensation circuit 912, the capacitive coupling circuit 913, and second compensation circuit 914 are configured to subject the AC signal outputted by the inverter 911 to energy conversion;

the rectifier 915 is configured to convert the AC signal outputted by the second compensation circuit 914 into a DC signal and output the DC signal to the wirelessly charged battery 15 or wirelessly charged battery 24 for charging.

Figure 10:
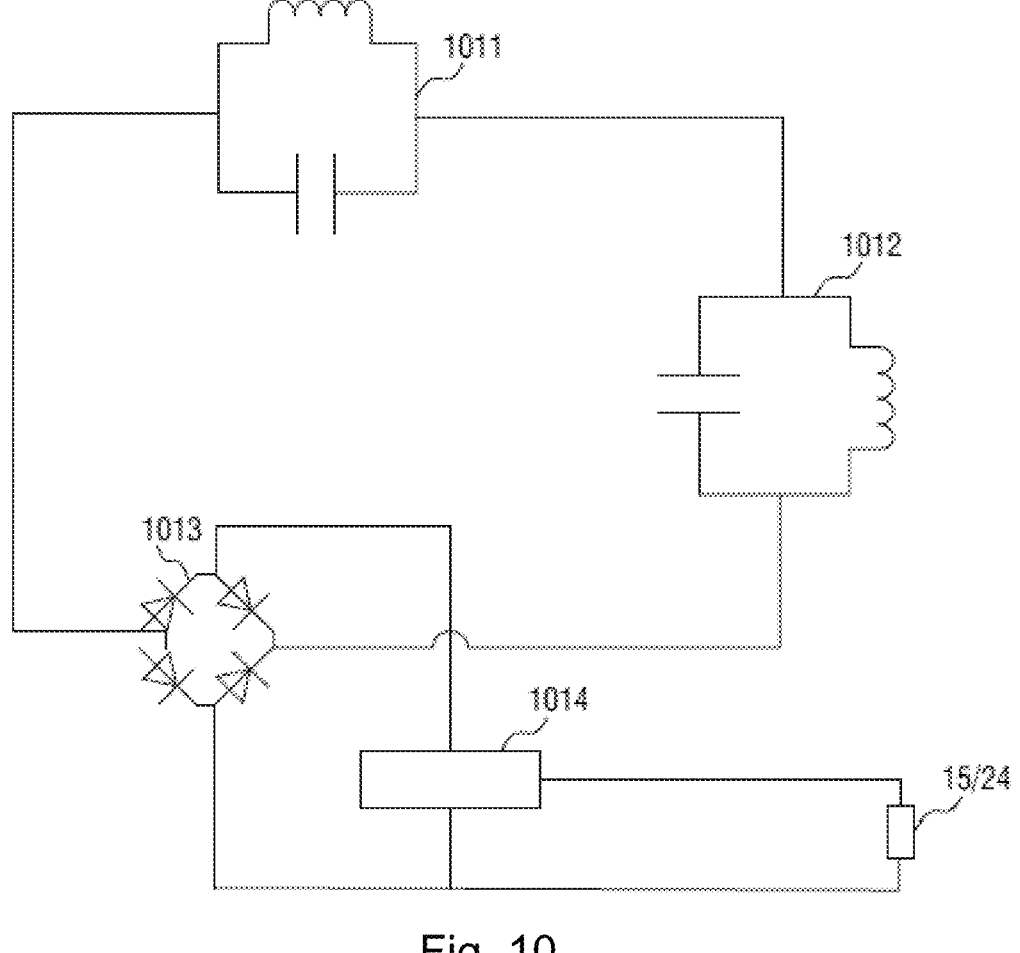
FIG. 10 is a schematic structural diagram of a charging module provided in an aspect of the present disclosure.

FIG. 10 is a schematic structural diagram of the charging module 813 provided in an aspect of the present disclosure, mainly comprising: at least one oscillation circuit (only two oscillation circuits, 1011 and 1012, are shown in FIG. 10), a rectifier 1013 and an LDO (Low DropOut regulator) 1014. The resonant frequency of each oscillation circuit separately corresponds to a transmission frequency of a wireless charging transmission coil (e.g., 10 MHz, 5 MHz, etc.), wherein, after series connection of the at least one oscillation circuit, the two ends thereof are separately connected to AC input ends of the rectifier 1013, a DC output end of the rectifier 1013 is connected to an input end of the LDO 1014, and an output end of the LDO 1014 is connected to the wirelessly charged battery 15 or wirelessly charged battery 24, wherein:

each oscillation circuit is configured to separately receive a power signal sent by a wireless charging transmission coil of a corresponding frequency and output the power signal to the rectifier 1013;

the rectifier 1013 is configured to convert the AC signal outputted by the oscillation circuit into a DC signal, and send the converted DC signal to the LDO 1014;

the LDO 1014 is configured to convert a voltage of the DC signal outputted by the rectifier 1013 into a voltage of the wirelessly charged battery 15 or wirelessly charged battery 24 and then output same to the wirelessly charged battery 15 or wirelessly charged battery 24.

In actual application, a turn-off threshold of the LDO 1014 may be set according to actual needs; for example, the turn-off threshold of the LDO 1014 may be set at 10 V, and when the output voltage of the LDO 1014 exceeds the turn-off threshold, the LDO 1014 and the rectifier 1013 are turned off. In addition, when designing the circuit shown in FIG. 10, it must be ensured that the loop has high resistance so as not to affect the B1 field properties of the MRI system; at the same time, the circuit design must enable operation at both high and low voltages, for example in the range of 3 V-10 V. This is because, when a supercapacitor is used as the wirelessly charged battery 15 or wirelessly charged battery 24, the range of voltage variation of the supercapacitor might be large.

In an optional aspect, to save charge in the wirelessly charged battery 15 or 24, the signal generating module 13 or 22, when sending an analog signal of each mode, may continuously send the analog signal of this mode for a second length of time at intervals of a first length of time, for example: in the case of an analog signal of one mode, the analog signal of this mode is sent continuously for 1 ms (millisecond) at intervals of 1 s (second).

In actual application, when the MR receiving module determines that the charge level of the wirelessly charged battery 15 or 24 in the wireless squeeze ball is insufficient based on the analog signal of the third mode sent by the antenna module 14 or 23. No analog signal of a second mode of a second frequency sent by the antenna module 14 or 23 is received within a continuous preset length of time; then, it is determined that the wireless squeeze ball has been taken out of the scanning room. An alert is sent that the wireless squeeze ball has been taken out of the scanning room.

In an optional aspect, the position detection apparatus 10 for a wireless squeeze ball may further comprise an acoustic alert module or/and an optical alert module, the acoustic alert module or/and the optical alert module being electrically connected to the mode triggering module 12. When the mode triggering module 12 does not receive an induced voltage signal sent by the electromagnetic induction module 11 or/and does not receive a voltage sent by the voltage detector, the acoustic alert module or/and the optical alert module are triggered to send an acoustic or/and an optical signal.

In an optional aspect, the position detection apparatus 20 for a wireless squeeze ball may further comprise an acoustic alert module or/and an optical alert module, the acoustic alert module or/and the optical alert module being electrically connected to the mode triggering module 21. When the mode triggering module 21 does not receive a voltage sent by the voltage detector, the acoustic alert module or/and the optical alert module are triggered to send an acoustic or/and an optical signal.

In an optional aspect, the MRI system may further comprise an acoustic alert module or/and an optical alert module, the acoustic alert module or/and the optical alert module being electrically connected to the MR receiving module. When the MR receiving module detects that the wireless squeeze ball has entered the interior of the body coil from outside the tubular body, or/and the charge level of the wirelessly charged battery 15 or 24 of the wireless squeeze ball is insufficient, the acoustic alert module or/and the optical alert module may be triggered to send an acoustic or/and an optical signal.

Furthermore, the position detection apparatus 10 or 20 for a wireless squeeze ball may perform self-testing periodically to discover faults promptly. During self-testing, the mode triggering module 12 or 21 receives a self-test signal sent by a self-testing module built into the wireless squeeze ball, for example, a signal indicating that the power supply voltage is too low or the squeezing function is abnormal, etc. The mode triggering module 12 or 21 outputs a preset trigger signal based on the self-test signal sent by the self-testing module, the trigger signal corresponding to the self-test signal. The signal generating module 13 or 22 generates an analog signal of a mode corresponding to the self-test signal based on the received trigger signal. It sends it out via the antenna module 14 or 23. The MR receiving module of the MRI system receives and then decodes the signal and issues a corresponding alert or displays an error prompt to an operator so that the operator can perform maintenance or replace the corresponding component.

The aspects of the present disclosure have the following beneficial technical effects:

1. The position of the wireless squeeze ball can be detected in real time so that the MRI system can promptly learn position change information of the wireless squeeze ball to promptly issue a corresponding alert according to the position of the wireless squeeze ball and the current MRI scan state, thus helping to improve the MRI system's operating efficiency as well as the patient's experience.

2. There is no need to add new hardware at the MRI system end; only a software update is required.

3. Power is supplied to modules in the wireless squeeze ball position detection apparatus using a wirelessly charged battery, so charging is convenient.

Aspects of the present disclosure further propose an MRI system, which may comprise the position detection apparatus 10 for a wireless squeeze ball, or the position detection apparatus 20 for a wireless squeeze ball, or the wireless squeeze ball system provided in the aspects above.

The above are merely preferred aspects of the present disclosure that are not intended to limit. Any amendments, equivalent substitutions or improvements, etc., made within the spirit and principles of the present disclosure shall be included in the scope of protection thereof.

The invention claimed is:

1. A position detection apparatus for a wireless squeeze ball, the apparatus being located in the wireless squeeze ball, comprising:

an electromagnetic induction module;

a mode triggering module;

a signal generating module; and an antenna module, wherein the electromagnetic induction module comprises: a B0 field electromagnetic inductor, a low-pass filter and an amplifier, the B0 field electromagnetic inductor and the low-pass filter being electrically connected, the low-pass filter and the amplifier being electrically connected, and the amplifier and the mode triggering module being electrically connected, wherein the B0 field electromagnetic inductor and the antenna module share a coil, wherein:

the electromagnetic induction module and the mode triggering module are electrically connected, the mode triggering module and the signal generating module are electrically connected, and the signal generating module and the antenna module are electrically connected, the B0 field electromagnetic inductor is configured to detect a change in magnetic flux inside a coil, and send an induced voltage signal generated due to the change in magnetic flux to the amplifier via the low-pass filter, the amplifier is configured to amplify the voltage signal processed by the low-pass filter, and send the amplified voltage signal to the mode triggering module, the electromagnetic induction module is configured to send to the mode triggering module an induced voltage signal generated due to a change in magnetic field, the mode triggering module is configured to output a preset trigger signal based on the induced voltage signal sent by the electromagnetic induction module, the trigger signal corresponding to the induced voltage signal, and the signal generating module is configured to generate an analog signal of a first mode corresponding to the induced voltage signal based on the trigger signal, and send the analog signal of the first mode to an MR receiving module of a magnetic resonance imaging (MRI) system via the antenna module at a first frequency, so that the MR receiving module judges whether the wireless squeeze ball has entered an interior of a body coil from outside a tubular body of the MRI system, based on the analog signal of the first mode, wherein the first frequency is different from an MR signal frequency.

2. The position detection apparatus as claimed in claim 1, wherein the electromagnetic induction module is a Hall effect sensor or a reed switch.

3. The position detection apparatus as claimed in claim 1, wherein:

operation of the mode triggering module outputs a preset trigger signal based on the induced voltage signal sent by the electromagnetic induction module, the trigger signal corresponding to the induced voltage signal, comprises:

the mode triggering module receiving the induced voltage signal sent by the electromagnetic induction module, generating a digital signal of a first mode based on a pre-configured digital signal of a first mode corresponding to the induced voltage signal of the electromagnetic induction module, and sending the digital signal of the first mode to the signal generating module, and operation of the signal generating module generating an analog signal of a first mode corresponding to the induced voltage signal based on the received trigger signal, comprises:

the signal generating module receiving the digital signal of the first mode sent by the mode triggering module, and converting the digital signal of the first mode into a corresponding analog signal of a first mode.

4. The position detection apparatus as claimed in claim 1, wherein the apparatus further comprises:

a wirelessly charged battery electrically connected to the mode triggering module and the signal generating module separately.

5. The position detection apparatus as claimed in claim 4, wherein:

the wirelessly charged battery comprises: a supercapacitor and a voltage detector connected in parallel with the supercapacitor, the voltage detector sending a detected voltage of the supercapacitor to the mode triggering module, and the mode triggering module is further configured to output a preset trigger signal based on the voltage sent by the voltage detector, the trigger signal corresponding to the voltage, and the signal generating module generates an analog signal of a mode corresponding to the voltage sent by the voltage detector based on the trigger signal outputted by the mode triggering module, and sends the analog signal of this mode to the MR receiving module of the MRI system via the antenna module at a first frequency, so that: the MR receiving module judges a state of the wirelessly charged battery based on the analog signal of this mode.

6. The position detection apparatus as claimed in claim 5, wherein:

operation of the mode triggering module outputting a preset trigger signal based on the voltage sent by the voltage detector, the trigger signal corresponding to the voltage, comprises:

the mode triggering module receiving the voltage sent by the voltage detector, and upon detecting that the voltage is less than a preset threshold, determining that a charge level of the wirelessly charged battery is insufficient, generating a digital signal of a third mode based on a pre-configured digital signal of a third mode corresponding to insufficient charge level of the wirelessly charged battery, and sending the digital signal of the third mode to the signal generating module, and operation of the signal generating module generating an analog signal of a mode corresponding to the voltage sent by the voltage detector based on the trigger signal outputted by the mode triggering module, comprises:

the signal generating module receiving the digital signal of the third mode sent by the mode triggering module, and converting the digital signal of the third mode into a corresponding analog signal of a third mode.

7. A wireless squeeze ball system, wherein the system comprises:

a wireless charging apparatus; and a wireless squeeze ball comprising the position detection apparatus for a wireless squeeze ball as claimed in claim 4.

8. The system as claimed in claim 7, wherein:

the wireless charging apparatus comprises: a voltage converter, an oscillator and a charging module, the voltage converter and the oscillator being electrically connected, and the oscillator and the charging module being electrically connected, the voltage converter is configured to convert a voltage of a received external power signal to a voltage of a wirelessly charged battery, and send the converted power signal to the oscillator, and the oscillator is configured to transmit the power signal sent by the voltage converter, to the wirelessly charged battery of the wireless squeeze ball in the charging module.

9. The system as claimed in claim 8, wherein the charging module uses a capacitive power transfer (CPT) system.

10. The system as claimed in claim 8, wherein the charging module comprises:

at least one oscillation circuit;

a rectifier; and a low-dropout regulator (LDO), wherein:

a resonant frequency of each oscillation circuit separately corresponds to a transmission frequency of a wireless charging transmission coil, after series connection of the at least one oscillation circuit, two ends thereof are separately connected to AC input ends of the rectifier, a DC output end of the rectifier is connected to an input end of the LDO, and an output end of the LDO is connected to the wirelessly charged battery, each oscillation circuit is configured to separately receive a power signal sent by the wireless charging transmission coil of the corresponding frequency and output the power signal to the rectifier, the rectifier is configured to convert an AC signal outputted by the oscillation circuit into a DC signal, and send the converted DC signal to the LDO, and the LDO is configured to convert a voltage of the DC signal outputted by the rectifier into a voltage of the wirelessly charged battery and then output same to the wirelessly charged battery.

11. An MRI system, comprising the wireless squeeze ball system as claimed in claim 7.

12. An MRI system, comprising the position detection apparatus for a wireless squeeze ball as claimed in claim 1.

13. A position detection apparatus for a wireless squeeze ball, the apparatus being located in the wireless squeeze ball, comprising:

an electromagnetic induction module;

a mode triggering module;

a signal generating module; and an antenna module, wherein:

the electromagnetic induction module and the mode triggering module are electrically connected, the mode triggering module and the signal generating module are electrically connected, and the signal generating module and the antenna module are electrically connected, the electromagnetic induction module is configured to send to the mode triggering module an induced voltage signal generated due to a change in magnetic field, the mode triggering module is configured to output a preset trigger signal based on the induced voltage signal sent by the electromagnetic induction module, the trigger signal corresponding to the induced voltage signal, the signal generating module is configured to generate an analog signal of a first mode corresponding to the induced voltage signal based on the trigger signal, and send the analog signal of the first mode to an MR receiving module of a magnetic resonance imaging (MRI) system via the antenna module at a first frequency, so that the MR receiving module judges whether the wireless squeeze ball has entered an interior of a body coil from outside a tubular body of the MRI system, based on the analog signal of the first mode, wherein the first frequency is different from an MR signal frequency, the mode triggering module is further configured to periodically generate a digital signal of a second mode based on a pre-configured digital signal of a second mode, and send the generated digital signal of the second mode to the signal generating module, and the signal generating module is further configured to convert the digital signal of the second mode sent by the mode triggering module into an analog signal of a second mode, and send the analog signal of the second mode to the MR receiving module of the MRI system via the antenna module at a second frequency, so that the MR receiving module judges whether the wireless squeeze ball has been taken out of a scanning room based on the analog signal of the second mode, wherein the second frequency is different from the MR signal frequency and the first frequency.

14. The position detection apparatus as claimed in claim 13, further comprising:

a wirelessly charged battery electrically connected to the mode triggering module and the signal generating module separately.

15. The position detection apparatus as claimed in claim 14, wherein the wirelessly charged battery comprises a supercapacitor and a voltage detector connected in parallel with the supercapacitor, the voltage detector sending a detected voltage of the supercapacitor to the mode triggering module, and wherein the mode triggering module is further configured to output a preset trigger signal based on the voltage sent by the voltage detector, the trigger signal corresponding to the voltage, and the signal generating module generates an analog signal of a mode corresponding to the voltage sent by the voltage detector based on the trigger signal outputted by the mode triggering module, and sends the analog signal of this mode to the MR receiving module of the MRI system via the antenna module at a first frequency, so that: the MR receiving module judges a state of the wirelessly charged battery based on the analog signal of this mode.

16. The position detection apparatus as claimed in claim 15, wherein:

operation of the mode triggering module outputting a preset trigger signal based on the voltage sent by the voltage detector, the trigger signal corresponding to the voltage, comprises:

the mode triggering module receiving the voltage sent by the voltage detector, and upon detecting that the voltage is less than a preset threshold, determining that a charge level of the wirelessly charged battery is insufficient, generating a digital signal of a third mode based on a pre-configured digital signal of a third mode corresponding to insufficient charge level of the wirelessly charged battery, and sending the digital signal of the third mode to the signal generating module, and wherein operation of the signal generating module generating an analog signal of a mode corresponding to the voltage sent by the voltage detector based on the trigger signal outputted by the mode triggering module, comprises:

the signal generating module receiving the digital signal of the third mode sent by the mode triggering module, and converting the digital signal of the third mode into a corresponding analog signal of a third mode.

17. A wireless squeeze ball system, wherein the system comprises:

a wireless charging apparatus; and a wireless squeeze ball comprising the position detection apparatus for a wireless squeeze ball as claimed in claim 14.

18. An MRI system, comprising the position detection apparatus for a wireless squeeze ball as claimed in claim 13.

* * * * *